United States Patent
Feng et al.

(10) Patent No.: US 10,935,495 B2
(45) Date of Patent: Mar. 2, 2021

(54) DETECTION AND ANALYSIS METHOD FOR URINE-MODIFIED NUCLEOSIDE BASED ON SURFACE-ENHANCED RESONANCE RAMAN SPECTROSCOPY

(71) Applicant: Fujian Normal University, Fujian (CN)

(72) Inventors: Shangyuan Feng, Fujian (CN); Zuci Zheng, Fujian (CN); Qiwen Wang, Fujian (CN); Lan Wang, Fujian (CN); Duo Lin, Fujian (CN); Cuncheng Weng, Fujian (CN); Zufang Huang, Fujian (CN); Yongzeng Li, Fujian (CN); Rong Chen, Fujian (CN)

(73) Assignee: Fujian Normal University, Fujian (CN)

( * ) Notice: Subject to any disclaimer, the term of this patent is extended or adjusted under 35 U.S.C. 154(b) by 346 days.

(21) Appl. No.: 16/304,691

(22) PCT Filed: Sep. 18, 2016

(86) PCT No.: PCT/CN2016/099170
§ 371 (c)(1),
(2) Date: Nov. 27, 2018

(87) PCT Pub. No.: WO2017/201924
PCT Pub. Date: Nov. 30, 2017

(65) Prior Publication Data
US 2020/0326285 A1 Oct. 15, 2020

(30) Foreign Application Priority Data
May 27, 2016 (CN) .......................... 201610365125.3

(51) Int. Cl.
*G01N 21/65* (2006.01)
*G01N 33/493* (2006.01)

(52) U.S. Cl.
CPC ......... *G01N 21/658* (2013.01); *G01N 33/493* (2013.01)

(58) Field of Classification Search
CPC .......................... G01N 21/658; G01N 33/493
See application file for complete search history.

(56) References Cited

U.S. PATENT DOCUMENTS

2008/0254548 A1 10/2008 Bamdad et al.

FOREIGN PATENT DOCUMENTS

CN 103740363 4/2014

OTHER PUBLICATIONS

Koshida et al., "Urinary Modified Nucleosides as Tumor Markers in Cancer of the Urinary Organs or Female Genital Tract", Urological Research, Sep. 30, 1985, pp. 213-214.
(Continued)

*Primary Examiner* — Maurice C Smith
(74) *Attorney, Agent, or Firm* — JCIPRNET

(57) ABSTRACT

The present invention discloses a detection and analysis method for urine-modified nucleoside based on a surface-enhanced resonance Raman spectroscopy technology. In the method, a tumor marker modified nucleoside in the urine of a normal person and a cancer patient is extracted through the specificity of borophenylic acid gel; Au colloid is taken as an enhancing substrate to detect SERRS signals; and statistical analysis is conducted by using PLS-DA algorithms to establish a diagnosis and identification model for the SERRS of the urine-modified nucleoside. The model is used to discriminate that the to-be-detected urine-modified nucleoside belongs to the normal person or the cancer patient. After PLS-DA, the surface-enhanced resonance Raman spectroscopy data of the urine-modified nucleoside of the present invention has specificity of 96.9%, sensitivity of 98.2% and accuracy of 97.6%. The present invention has the charac-
(Continued)

teristic of rapid and objective detection, and can provide important reference for doctors to diagnose esophagus cancer.

9 Claims, 2 Drawing Sheets

(56) References Cited

OTHER PUBLICATIONS

Huang et al., "Non-invasive optical detection of esophagus cancer based on urine surface-enhanced Raman spectroscopy", Proceedings of SPIE, Sep. 2014, Cover page and pp. 923020-1-923020-6.
Huang et al., "The Application of SERS Spectroscopy in the Study of Human Body Fluid", Acta Laser Biology Sinica, Dec. 2012, pp. 481-485.
Feng et al., "Application of urinary nucleosides in the diagnosis and surgical monitoring colorectal cancer", Chin J Surg, May 2005, pp. 564-568.
Wang et al., "Diagnosis of Esophageal Tissue Based on Surface-Enhanced Raman Spectroscopy", Scientia Sinica Vitae, Dec. 31, 2013, pp. 525-532.
Li et al., "Statistical Analysis of Tissue Raman Spectroscopy", Acta Laser Biology Sinica, Feb. 2011, pp. 130-133, and 142.
"International Search Report (Form PCT/ISA/210)", dated Feb. 20, 2017, with English translation thereof, pp. 1-6.

DETECTION AND ANALYSIS METHOD FOR URINE-MODIFIED NUCLEOSIDE BASED ON SURFACE-ENHANCED RESONANCE RAMAN SPECTROSCOPY

CROSS-REFERENCE TO RELATED APPLICATION

This application is a 371 application of an international PCT application serial no. PCT/CN2016/099170, filed on Sep. 18, 2016, which claims priority to and the benefit of China Patent Application No. 201610365125.3, filed on May 27, 2016. The entirety of each of the above-mentioned patent applications is hereby incorporated by reference herein and made a part of this specification.

BACKGROUND OF THE INVENTION

1. Technical Field

The present invention relates to the field of biomedical optics, in particular to a detection and analysis method for urine tumor marker modified nucleoside based on surface-enhanced resonance Raman spectroscopy. The detection and analysis method relates to a detection method and a multi-variable statistical analysis method based on separation and purification of tumor markers by gel chromatographic columns and surface-enhanced resonance Raman spectroscopy (SERRS).

2. Description of the Related Art

Nucleoside is a metabolite of RNA in the body, and produces free normal nucleoside and modified nucleoside in RNA metabolism. The normal nucleoside can be recycled to produce nucleic acid, and thus is rarely discharged from the urine. The modified nucleoside lacks of corresponding kinase and cannot be recycled by the body, and thus most of the modified nucleoside is discharged out of the body along with the urine. Therefore, the displacement of the modified nucleoside in the urine can reflect the metabolism velocity of body cells. The change of the displacement of the modified nucleoside in the urine of healthy adults is small, indicating that the body can finely regulate the RNA metabolism. The proliferation of tumor cells is faster than that of normal cells, resulting in the increase of production and discharge of the modified nucleoside. Thus, the modified nucleoside is widely used as a tumor marker in medical diagnosis and study.

The gel chromatographic column technology is a rapid and simple separation analysis technology developed in the early years of the 1960s. Because of simple device, easy operation and no need of organic solvent, it has a high separation effect on macromolecules and macromolecules. At present, it has been widely used in the fields of biochemistry, molecular biology, bioengineering, molecular immunology and medicine. The technology is not only used in scientific experimental research, but also used in industrial production on a large scale. The present invention will extract tumor marker of modified nucleoside from the urine by means of excellent separation performance of the chromatographic column, and conducts detection and analysis in combination with a surface-enhanced resonance Raman spectroscopy technology.

The Raman spectroscopy technology is one of standard technologies for article identification and molecular detection. However, the conventional Raman spectroscopy has the disadvantages of weak Raman spectroscopy signal and easy interference by autofluorescence. Surface-enhanced Raman spectroscopy (SERS) detection utilizes the adsorption of the detected molecules with certain metals (such as Au, Ag, Cu, and Pt) with nano-roughness to increase the Raman scattering intensity of these molecules by $10^4$-$10^{15}$ times, and can effectively suppress autofluorescence signals. Such detection is a novel objective, rapid and nondestructive detection method superior to the conventional Raman spectroscopy, and will probably help doctors to improve the speed and accuracy of diagnosis. The SERS technology has the advantages of high spatial resolution, high sensitivity, rich information content, etc., and has been widely used in the fields of substance identification, detection of molecular structures, etc. However, the surface-enhanced resonance Raman spectroscopy (SERRS) technology not only has the advantages of ordinary SERS, but also realizes surface plasmon resonance between the excitation light of a special wave band and the detected objects, which can further improve the detection sensitivity of the spectroscopy.

At present, domestic and foreign scholars detect the urine mainly by directly conducting Raman spectroscopy detection and analysis on the obtained urine samples, but components in the urine are complicated and are interfered by many factors. Therefore, it is difficult to achieve an ideal detection effect.

BRIEF SUMMARY OF THE INVENTION

The purpose of the present invention is to provide a detection and analysis method for urinary modified nucleoside based on surface-enhanced resonance Raman spectroscopy in view of the defects and problems in the existing urine surface-enhanced Raman spectroscopy analysis, so as to provide a rapid and objective evaluation standard for distinguishing the SERRS of urine-modified nucleoside of normal healthy persons and cancer patients. This method is as follows: the tumor marker of modified nucleoside in the urine from a normal person and a cancer patient is extracted and purified at first through boric acid gel chromatographic columns; a surface-enhanced resonance Raman spectroscopy (SERRS) signal of the tumor marker is detected by taking Au colloid as an enhancing substrate and taking laser with a wavelength of 785 nm as exciting light; and a statistical analysis method is combined for detection and analysis.

To achieve the above purpose, the present invention adopts the following technical solution:

A detection and analysis method for urine-modified nucleoside based on surface-enhanced resonance Raman spectroscopy comprises the following steps:

(1) taking a urine sample for centrifugal treatment, wherein the urine sample comprising a normal group and an abnormal group, the normal group comprises urine samples of healthy persons and the abnormal group comprises urine samples of cancer patients; and extracting tumor marker modified nucleoside in the urine samples by using borophenylic acid gel chromatographic columns to obtain a urine-modified nucleoside of the normal group and the abnormal group;

(2) uniformly mixing the urine-modified nucleoside of the normal group and the abnormal group with Au colloid at equal volume to obtain a mixed sample of the normal group and the abnormal group; and conducting a surface-enhanced resonance Raman spectroscopy measurement on the urine-modified nucleoside after the mixed sample is naturally dried at 4° C., to respectively obtain a surface-enhanced resonance Raman spectroscopy data of the urine-modified nucleoside of the normal group and the abnormal group;

(3) establishing a surface-enhanced resonance Raman spectroscopy diagnosis and identification model of urine-modified nucleoside for discriminating that the urine-modified nucleoside belongs to a healthy person or belongs to a cancer patient through partial least square and linear discriminant analysis according to the above obtained surface-enhanced resonance Raman spectroscopy data of the urine-modified nucleoside of the normal group and the abnormal group;

(4) taking the urine sample of a to-be-detected person; obtaining surface-enhanced resonance Raman spectroscopy data of the to-be-detected urine-modified nucleoside in accordance with the method in steps (1) and (2); analyzing through the partial least square and the linear discriminant analysis and then substituting the diagnosis and identification model established in the step (3); and discriminating that the to-be-detected urine-modified nucleoside belongs to the healthy person or belongs to the cancer patient.

Further, in the step (2), the mixed sample formed by the urine-modified nucleoside and the Au colloid is dropwise added to sheet metal with a purity of 99.99%; the surface-enhanced resonance Raman spectroscopy of the urine-modified nucleoside is obtained through 785 nm laser excitation; and the taking range of Raman spectroscopy is the wave number range of 500-1800 $cm^{-1}$.

Further, the urine sample in the step (1) is pretreated as follows: overnight empty-stomach human urine at 7-8 a.m. morning is taken; and after the urine is centrifuged, a clarified upper-layer of the urine is collected.

The urine-modified nucleoside is extracted from the pretreated urine in accordance with the following method:

loading borophenylic acid gel in a glass chromatographic column to form an affinity chromatographic column, washing the gel once with 30-35 mL ammonium acetate with a molar concentration of 0.25 mol/L, and activating and balancing the gel, with the pH of the ammonium acetate being 8.5;

adding 1 mL of the centrifuged clarified urine into chromatographic column, and then washing the gel for the second time with 20-25 mL ammonium acetate with a molar concentration of 0.25 mol/L and 3-4 mL methanol aqueous solution (volume ratio of 1:1);

finally, eluting with 25 mL methanol aqueous solution containing 0.1 mol/L formic acid (volume ratio of 1:1), collecting eluent, evaporating and concentrating to 1 mL to obtain the urine-modified nucleoside.

Further, the preparation method of the Au colloid is specifically as follows: adding $1 \times 10^{-3}$ g/mL chloroauric acid solution to water in accordance with a volume ratio of 1:9; stirring uniformly and heating until the water is boiled; then quickly adding trisodium citrate solution with a mass concentration of 1%, with the adding volume of the trisodium citrate solution being 10% of the chloroauric acid solution; heating continuously and stirring to obtain the wine red Au colloid; centrifuging after the Au colloid is cooled; discarding supernatant; and collecting lower-layer of the concentrated Au colloid.

The present invention for distinguishing urine-modified nucleoside must be realized by a diagnosis model. Therefore, an SERRS diagnosis and identification model of the urine-modified nucleoside shall be established to judge that the urine-modified nucleoside belongs to the normal person or belongs to the cancer patient. Before establishing the spectral identification and diagnosis database model, the area of the SERRS of the urine-modified nucleoside should be normalized to remove the influence caused by small differences in experimental test conditions. In modeling, considering some individual differences in different patients, a sufficient number of confirmed cases of SERRS must be collected to establish a spectroscopy database for statistical purposes. The surface-enhanced resonance Raman spectroscopy recognition mode for discriminating that human urine-modified nucleoside belongs to the normal person or the cancer patient is formed by the surface-enhanced Raman spectroscopy database of the urine-modified nucleoside of the confirmed cases and the healthy persons. Based on the establishment of the database, a best identification mode for the SERRS of the urine nucleoside of the normal person and the SERRS of the urine nucleoside of the cancer patient in the database is given by the partial least square (PLS) and the linear discriminant analysis (LDA). The threshold condition for realizing pattern recognition becomes the diagnostic condition.

The SERRS spectral diagnosis and recognition model of the present invention is established by a combination of the partial least square and the linear discriminant analysis (PLS-DA). The partial least square (PLS) is a novel and efficient method for multi-variable statistical analysis. It can realize the regression modeling method of multi-dependent variable to multi-independent variable, and can simultaneously implement regression modeling, data structure simplification and correlation analysis between two sets of variables. The partial least square can better solve the problems which cannot be solved by general principal component analysis (PCA). The partial least square adopts a method of decomposing variables X and Y and simultaneously extracting components (or called as factors) from the variables X and Y. The high-dimensional Raman spectroscopy data is subjected to dimensionality reduction through this method, and the factors are arranged from large to small in terms of their correlation. The linear discriminant analysis (LDA) extracts low-dimensional features having the most discriminant capacity from a high-dimensional feature space. The features help to gather all samples of the same category together as much as possible, and separate samples of different categories as much as possible. PLS and LDA have their own strengths. They capture different statistical features and are suitable for different specific situations. Thus, it is very necessary for the present invention to combine two algorithms of PLS and LDA.

When the diagnosis and identification model is established in the present invention, the specific algorithm of PLS-DA is as follows:

① the surface-enhanced resonance Raman spectroscopies of the urine-modified nucleoside of the normal group and the abnormal group are fitted by a higher-order polynomial to eliminate fluorescent background interference;

② the surface-enhanced resonance Raman spectroscopies of the urine-modified nucleoside of the normal group and the abnormal group without fluorescent background interference are normalized to eliminate experimental system errors;

③ the surface-enhanced resonance Raman spectroscopies of the urine-modified nucleoside of the normal group and the abnormal group after treatment of Matlab software in ① and ② are modeled and analyzed through the partial least square;

④ selecting the first three partial least square scores with the most significant differences as principal components by using T test based on the step ③; then conducting discriminant analysis on the three principal components by using the linear discriminant analysis; obtaining a posterior probability corresponding to each sample of the normal group and the abnormal group from the output result of the linear discriminant analysis; obtaining a scatter distribution map of the posterior probability corresponding to each sample; and determining the posterior probability for distinguishing the surface-enhanced resonance Raman spectroscopies of the urine-modified nucleoside of the normal group and the abnormal group, i.e., a threshold.

The diagnosis and identification model of the present invention is applied in clinical diagnosis as follows: the urine sample of the to-be-detected person is taken; the urine-modified nucleoside is extracted in accordance with the above method; then the SERRS of the to-be-detected person is measured; the detected SERRS is substituted into the established diagnosis and identification model of the surface-enhanced resonance Raman spectroscopies of the urine-modified nucleoside in the present invention; mode discrimination analysis of the urine-modified nucleoside for the cancer patient and the normal person is conducted according to the diagnosis condition; and then diagnosis of the SERRS is realized.

The present invention adopts the above technical solution. Detection and analysis of SERRS are conducted on the tumor marker of modified nucleoside in the urine through the surface-enhanced resonance Raman spectroscopy technology in which Au nano particles are taken as the enhancing substrates and the 785 nm laser is taken as exciting light. This technical solution has not been reported in pertinent literature up to now. The method respectively centrifuges the urine of the normal person and the cancer patient, removes the precipitate, takes the supernatant, extracts and purifies modified nucleoside in the urine through the affinity chromatographic column of the gel, and realizes rapid detection and identification for the cancer patient through SERRS analysis on the nucleoside of the urine by using the surface-enhanced resonance Raman spectroscopy (SERRS) as a detection means. Extraction of the urine-modified nucleoside and the pretreatment of the sample in the present invention takes 1 h. The spectral detection time is only 10 seconds. The present invention has the advantages of simplicity, rapidness and strong reliability. Meanwhile, the SERRS technology (taking Au colloid as an enhancing substrate and taking laser with a wavelength of 785 nm as exciting light) can obtain strong Raman spectroscopy signals when the sample is illuminated under very low laser power, thereby avoiding damage to biomolecules by high power laser. The spectroscopy signals have good repeatability. The SERRS database of the urine-modified nucleoside is established according to the obtained surface-enhanced resonance Raman spectroscopy of the urine-modified nucleoside of the normal person and the cancer patient, and the multi-variable statistical analysis method is used, so as to provide a rapid and objective evaluation standard for distinguishing the SERRS of urine-modified nucleoside of normal healthy persons and cancer patients.

The SERRS database of the urine-modified nucleoside of the present invention includes surface-enhanced Raman spectroscopies of the urine nucleoside of 32 normal persons and the urine nucleoside of 55 diagnosed patients with esophagus cancer. After PLS-DA, the surface-enhanced resonance Raman spectroscopy data of the urine-modified nucleoside has specificity of 96.9%, sensitivity of 98.2% and accuracy of 97.6%.

The substitute of the urine-modified nucleoside may be other types of tumor markers in urine, blood, saliva, semen and tissue homogenate.

BRIEF DESCRIPTION OF THE DRAWINGS

The present invention is described below in detail in combination with the drawings and specific embodiments.

In FIG. 3 and FIG. 4, a region above a straight line P=0.5 is a region of the urine-modified nucleoside of a patient with esophagus cancer, and a region below the straight line P=0.5 is a region of the urine nucleoside of a normal person.

DETAILED DESCRIPTION OF THE INVENTION

Specific implementation cases of the present invention obtain informed consent of the patients. Specific implementation details of the present invention are illustrated as follows:

(1) Pretreatment of Urine Sample

Overnight empty-stomach human urine of normal persons (32 persons) and cancer patients (55 persons) at a.m. 7-8 is taken; the urine is put into a centrifuge for centrifugation; rotational speed is set as 10000 revolutions per minute; and centrifugation is conducted for 10 minutes. Lower-layer precipitate is discarded, and upper-layer clarified urine is taken. An abnormal group (urine of patients with esophagus cancer) and a normal group (urine of normal healthy persons) are respectively obtained through this method.

(2) Extraction of Urine-Modified Nucleoside

Borophenylic acid gel is loaded in a glass chromatographic column to form an affinity chromatographic column to extract the urine; the gel is activated and balanced through 35 ml ammonium acetate (pH 8.5) with 0.25 mol/L; 1 ml centrifuged urine is loaded to the column. Then, the gel is washed for the second time with 20 mL ammonium acetate of 0.25 mol/L and 3 ml methanol aqueous solution (volume ratio of 1:1); the nucleoside is eluted with 25 mL methanol aqueous solution containing 0.1 mol/L formic acid (volume ratio of 1:1); and eluent is evaporated and concentrated to 1 mL to obtain the urine-modified nucleoside for use.

(3) Preparation of Au colloid 10 ml chloroauric acid solution ($1\times10^{-3}$ g/mL) is added to 90 ml purified water and uniformly stirred and heated until the water is boiled. Then, 1 ml trisodium citrate solution (1%) is quickly added, and continuously heated and stirred for 15 minutes to obtain wine red Au colloid. After cooled, the Au colloid is centrifuged with a high-speed centrifuge for 10 minutes. The rotational speed is set as 15000 revolutions per minutes. The Au colloid is layered. The supernatant is discarded, and lower-layer concentrated Au colloid is taken and sealed away from light at room temperature for use.

(4) Preparation of Mixed Liquid of Au Colloid-Urine-Modified Nucleoside

50 μL urine-modified nucleoside samples are taken out of the normal group (normal healthy persons) by using a pipette, and added to a test tube treated with sterile disinfection. 50 μL prepared centrifuged high-concentration Au colloid is respectively added to the test tube with the pipette.

The mixed solution of nucleoside is fully stirred so that the urine-modified nucleoside and the Au colloid are uniformly mixed as much as possible to prepare the mixed solution of Au colloid-urine-modified nucleoside of the normal group.

The mixed solution of Au colloid-urine nucleoside of the abnormal group (cancer patients) is prepared through the same method.

(5) Sample Detecting Process of Surface-Enhanced Resonance Raman Spectroscopy

Figure 1:
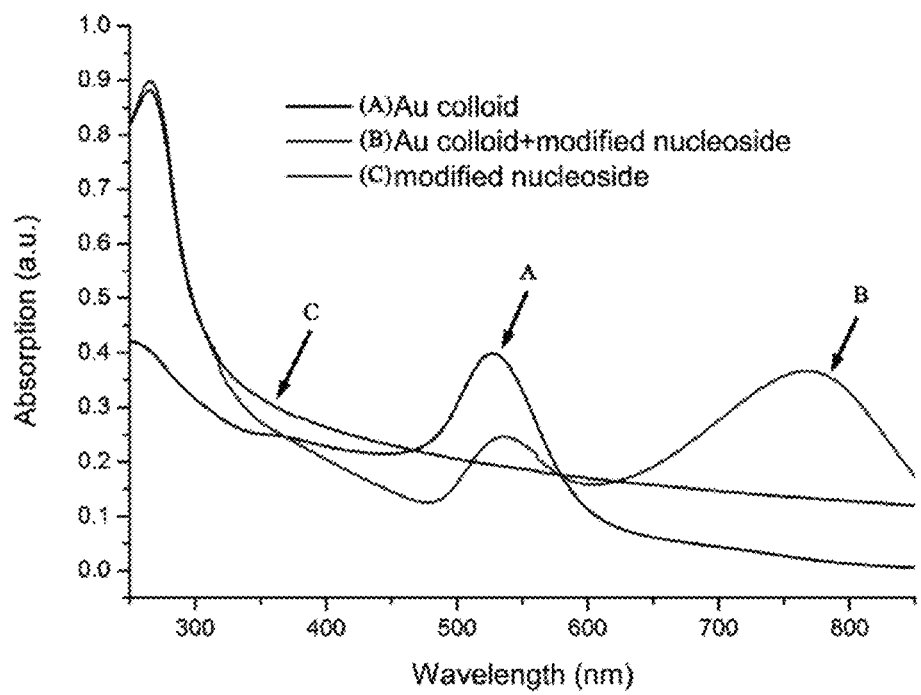
FIG. 1 is an absorption spectrogram of Au colloid, urine-modified nucleoside and a mixture of Au colloid and urine-modified nucleoside.
Figure 2:
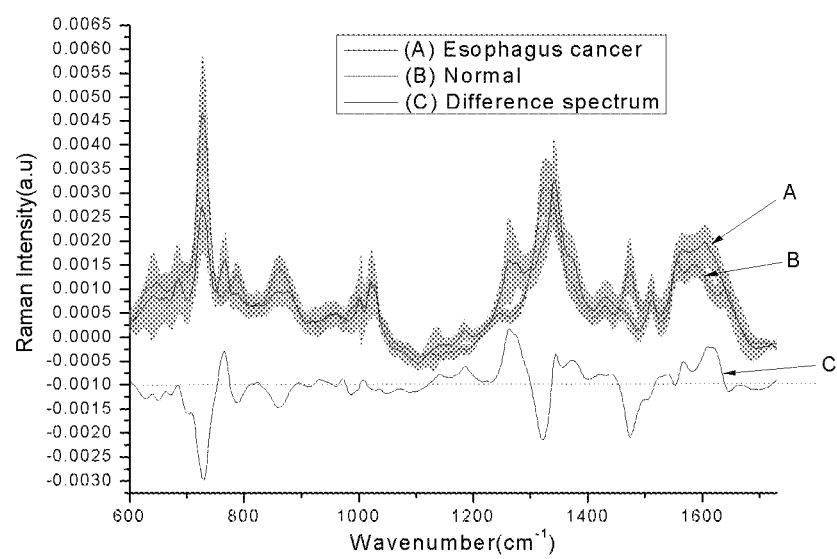
FIG. 2 shows an average SERRS and difference spectroscopy of the urine-modified nucleoside of a normal person and a cancer patient.

The mixed solution of mixed Au colloid-urine-modified nucleoside is moved to a high-purity metal sample platform with the pipette, and naturally aired. The sample is detected through a confocal microscopical Raman spectrometer to obtain the SERRS spectroscopy of the urine nucleoside. The detection focus is on the range of the wave number of 600-1730 $cm^{-1}$. Measurement parameters are set: integration time, 10 s; excitation wavelength, 785 nm; and excitation optical power, 5 mw. As shown in FIG. 1, laser with a wavelength of 785 nm is just located in the surface plasmon resonance absorption peak of the mixture of Au colloid and the modified nucleoside, so near infrared laser of 785 nm can excite strong SERRS signals. Test objects of the present embodiment include surface-enhanced Raman spectroscopies of the urine nucleoside of 32 normal persons and the urine-modified nucleoside of 55 diagnosed cancer patients.

(6) Establishment of Surface-Enhanced Resonance Raman Spectroscopy Diagnosis and Identification Model for Discriminating Urine-Modified Nucleoside of Normal Persons and Patients with Esophagus Cancer The urine-modified nucleoside must be discriminated and detected through a diagnosis model. Therefore, an SERRS diagnosis and identification model of the urine-modified nucleoside shall be established to judge that the urine-modified nucleoside belongs to the normal person or belongs to the cancer patient. The identification model is formed by the surface-enhanced Raman spectroscopy database of the urine-modified nucleoside of the confirmed cases and the healthy persons. On the basis of establishing the database, a best identification mode for the surface-enhanced resonance Raman spectroscopy of the urine nucleoside of the normal person and the surface-enhanced Raman spectroscopy of the urine nucleoside of the patient with esophagus cancer in the database is given through the partial least square (PLS) and the linear discriminant analysis (LDA), while the threshold condition for realizing mode identification becomes a diagnosis condition.

The computational process of the present embodiment using PLS-DA algorithms is as follows:

① The SERRS of the urine-modified nucleoside of the normal group (32 normal persons) and the SERRS of the urine-modified nucleoside of the abnormal group (55 patients with esophagus cancer) are fitted through a higher-order polynomial to eliminate fluorescent background interference;

② the SERRS of each of the urine-modified nucleoside of the normal group and the abnormal group without fluorescent background interference are normalized to eliminate experimental system errors;

③ principal components LV1, LV2 and LV3 are calculated through PLS standard algorithm for the SERRS of each of the urine-modified nucleoside;

④ LDA is conducted on the principal components LV1, LV2 and LV3; and finally, a posterior probability (P value) corresponding to each sample is obtained from the output result of LDA, and a scatter distribution map of the posterior probability corresponding to each sample is obtained;

⑤ The posterior probability distribution of the SERRS of the urine-modified nucleoside of 32 normal persons and 55 patients with esophagus cancer is the measurement and analysis result of the present invention, which can provide a diagnosis basis for doctors. After LDA calculation in the present invention, a best straight line for distinguishing and diagnosing the SERRS of the urine nucleoside of the normal persons and the patients with esophagus cancer is determined as the posterior probability P=0.5. Then, the equation actually defines that this straight line effectively separates the point set distribution of the urine nucleoside of the normal persons from the point set distribution of the urine nucleoside of the patients with esophagus cancer on a two-dimensional coordinate plane formed by the posterior probability and the sample number. This straight line is equivalent to setting a threshold, and this threshold is the diagnosis condition.

In specific clinical application, the urine-modified nucleoside of the patients is extracted; the posterior probability is calculated through the PLS-DA algorithms for the surface-enhanced resonance Raman spectroscopy data of the urine-modified nucleoside of the patients; and the posterior probability is compared with the threshold to discriminate that the urine-modified nucleoside of the patient belongs to the healthy person or belongs to the cancer patient, so as to realize quick and nondestructive detection for the urine-modified nucleoside of the patient.

Clinical Application Example 1

Figure 3:
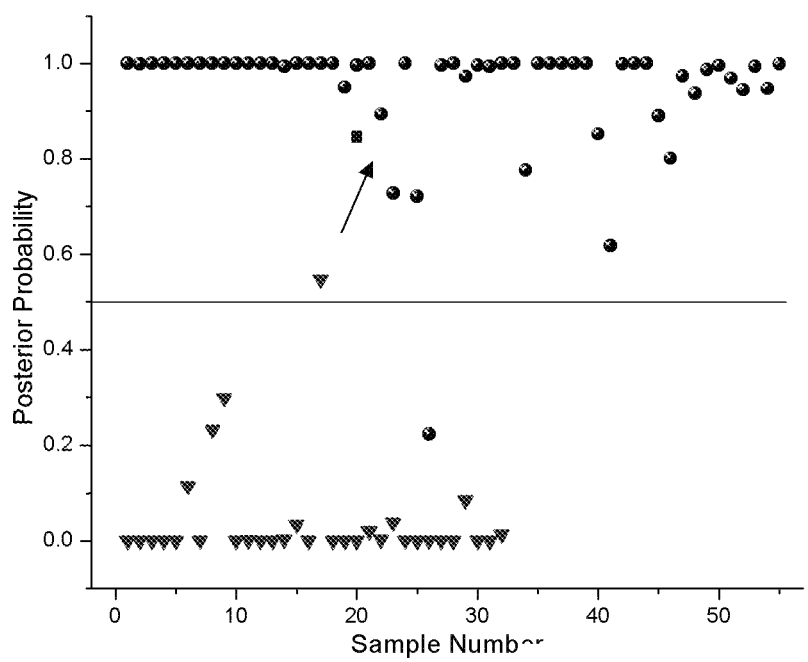
FIG. 3 is an SERRS diagnosis result of the present invention for embodiment 1.

Liao X X, male, 52 years old, pathological diagnosis of myeloid highly and moderately differentiated squamous cell carcinoma. Cancer tissue covers the whole layer. Cancer embolus is seen in the blood vessel, staged as T4, N1 and Mx. Double-blind detection is conducted by the present invention. The posterior probability P=0.845 for the SERRS of the urine-modified nucleoside of the patient is calculated through the PLS-DA model. The calculation result shows that the patient is judged as a patient with esophagus cancer. FIG. 3 is the diagnosis result of the application example 1. The figure shows the posterior probability corresponding to the surface-enhanced Raman scattering of the urine-modified nucleoside of each sample. In the figure, circular points represent the patients with esophagus cancer, triangular pointed points represent normal healthy persons, and a square point represents a to-be-identified patient.

In FIG. 3, the SERRS of the urine-modified nucleoside of the normal healthy persons and the patients with esophagus cancer forms the diagnosis and identification model of the present invention. The model determines that a best straight line for distinguishing and diagnosing the SERRS of the urine nucleoside of the normal persons and the patients with esophagus cancer is the posterior probability P=0.5. A region above a straight line P=0.5 is a region of the urine-modified nucleoside of a patient with esophagus cancer, and a region below the straight line P=0.5 is a region of the urine nucleoside of a normal person.

The application example extracts the urine-modified nucleoside of the patient, determines the SERRS of the urine-modified nucleoside and calculates the posterior probability P=0.845. The patient can be judged as a cancer patient through the diagnosis and identification model.

Clinical Application Example 2

Figure 4:
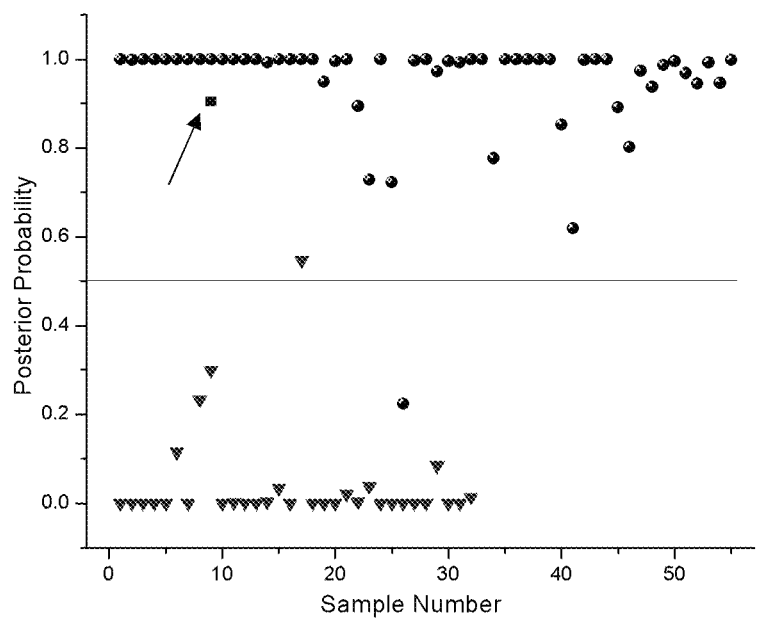
FIG. 4 is an SERRS diagnosis result of the present invention for embodiment 2.

Zou X X, male, 61 years old, pathological diagnosis of fungating type highly and moderately differentiated squamous cell carcinoma. Cancer tissue covers the muscular layer. Cancer embolus is seen in the vessel, staged as T2, N0 and Mx. Double-blind detection is conducted by the present invention. The posterior probability P=0.904 for the SERRS of the urine-modified nucleoside of the patient is calculated through the PLS-DA model. The calculation result shows that the patient has cancer. FIG. 4 is the diagnosis result of the application example 2. The figure shows the posterior probability corresponding to the surface-enhanced Raman scattering of the urine-modified nucleoside of each sample. In the figure, circular points represent patients with esophagus cancer, triangular pointed points represent the normal healthy persons, and a square point represents a to-be-identified patient.

What is claimed is:

1. A detection and analysis method for urine-modified nucleoside based on surface-enhanced resonance Raman spectroscopy, comprising following steps of:
   (1) taking a urine sample for centrifugal treatment, wherein the urine sample comprising a normal group and an abnormal group, the normal group comprises urine samples of healthy persons and the abnormal group comprises urine samples of cancer patients; and extracting tumor marker modified nucleoside in the urine samples by using borophenylic acid gel chromatographic columns to obtain a urine-modified nucleoside of the normal group and the abnormal group;
   (2) uniformly mixing the urine-modified nucleoside of the normal group and the abnormal group with Au colloid at equal volume to obtain a mixed sample of the normal group and the abnormal group; and conducting a surface-enhanced resonance Raman spectroscopy measurement on the urine-modified nucleoside of the normal group and the abnormal group after the mixed sample is naturally dried, to respectively obtain a surface-enhanced resonance Raman spectroscopy data of the urine-modified nucleoside of the normal group and the abnormal group;
   (3) establishing a surface-enhanced resonance Raman spectroscopy diagnosis and identification model of urine-modified nucleoside for discriminating that the urine-modified nucleoside of the normal group and the abnormal group belongs to a healthy person or belongs to a cancer patient through a partial least square and a linear discriminant analysis according to the surface-enhanced resonance Raman spectroscopy data of the urine-modified nucleoside of the normal group and the abnormal group obtained above;
   (4) taking a urine sample of a to-be-detected person; obtaining a surface-enhanced resonance Raman spectroscopy data of a to-be-detected urine-modified nucleoside in accordance with the method in the steps (1) and (2); analyzing through the partial least square and the linear discriminant analysis and then substituting the surface-enhanced resonance Raman spectroscopy diagnosis and identification model of urine-modified nucleoside established in the step (3); and discriminating that the urine sample of the to-be-detected urine-modified nucleoside belongs to the healthy person or belongs to the cancer patient.

2. The detection and analysis method for urine-modified nucleoside based on surface-enhanced resonance Raman spectroscopy according to claim 1, wherein in the step (2), the mixed sample of the normal group and the abnormal group formed by the urine-modified nucleoside of the normal group and the abnormal group and the Au colloid is dropwise added to sheet metal with a purity of 99.99%; the surface-enhanced resonance Raman spectroscopy of the urine-modified nucleoside of the normal group and the abnormal group is obtained by 785 nm laser excitation; and a taking range of the surface-enhanced resonance Raman spectroscopy is a wave number range of 500-1800 $cm^{-1}$.

3. The detection and analysis method for urine-modified nucleoside based on surface-enhanced resonance Raman spectroscopy according to claim 1, wherein the urine sample in the step (1) is pretreated as follows: an overnight empty-stomach human urine at is taken at 7-8 a.m. morning is taken; and after the urine sample is centrifuged, a clarified upper-layer of the urine sample is collected.

4. The detection and analysis method for urine-modified nucleoside based on surface-enhanced resonance Raman spectroscopy according to claim 3, wherein the urine-modified nucleoside of the normal group and the abnormal group is extracted as follows:
   loading a borophenylic acid gel in a glass chromatographic column to form an affinity chromatographic column, washing the borophenylic acid gel once with 30-35 mL ammonium acetate with a molar concentration of 0.25 mol/L, and activating and balancing the borophenylic acid gel, a pH of the ammonium acetate is 8.5;
   adding 1 mL of centrifuged clarified urine into chromatographic column, and then washing the gel for the second time with 20-25 mL ammonium acetate with a molar concentration of 0.25 mol/L and 3-4 mL methanol aqueous solution;
   finally, eluting with 25 mL methanol aqueous solution containing 0.1 mol/L formic acid, collecting eluent, evaporating and concentrating to 1 mL to obtain the urine-modified nucleoside.

5. The detection and analysis method for urine-modified nucleoside based on surface-enhanced resonance Raman spectroscopy according to claim 1, wherein the Au colloid in the step (2) is prepared by reducing chloroauric acid solution with trisodium citrate.

6. The detection and analysis method for urine-modified nucleoside based on surface-enhanced resonance Raman spectroscopy according to claim 5, wherein a preparation method of the Au colloid is specifically as follows: adding $1\times10^{-3}$ g/mL of a chloroauric acid solution to water in accordance with a volume ratio of 1:9; stirring uniformly and heating until the water is boiled; then quickly adding trisodium citrate solution with a mass concentration of 1%, with an adding volume of the trisodium citrate solution being 10% of the chloroauric acid solution; heating continuously and stirring to obtain the wine red Au colloid; centrifuging after the Au colloid is cooled; discarding a supernatant of the Au colloid; and collecting a lower-layer of the concentrated Au colloid.

7. The detection and analysis method for urine-modified nucleoside based on surface-enhanced resonance Raman spectroscopy according to claim 1, wherein the diagnosis and identification model established in the step (3) is conducted through a statistical analysis using a database of step (2); and the statistical analysis conducts a discriminant calculation using the partial least square and the linear discriminant analysis, and a specific algorithm is as follows:
   ① the surface-enhanced resonance Raman spectroscopy data of the urine-modified nucleoside of the normal group and the abnormal group is fitted through a higher-order polynomial to eliminate a fluorescent background interference;

②  the surface-enhanced resonance Raman spectroscopy data of the urine-modified nucleoside of the normal group and the abnormal group without the fluorescent background interference are normalized to eliminate experimental system errors;

③ the surface-enhanced resonance Raman spectroscopy data of the urine-modified nucleoside of the normal group and the abnormal group after treatment of Matlab software in ① and ② are modeled and analyzed through the partial least square;

④ selecting the first three scores of the partial least square with the most significant differences as three principal components by using T test based on ③; then conducting discriminant analysis on the three principal components by using the linear discriminant analysis; obtaining a posterior probability P value corresponding to each of the urine sample of the normal group and the abnormal group from an output result of the linear discriminant analysis; obtaining a scatter distribution map of the posterior probability corresponding to each of the urine sample; and determining a threshold of the posterior probability for distinguishing the surface-enhanced resonance Raman spectroscopy data of the urine-modified nucleoside of the normal group and the abnormal group.

8. The detection and analysis method for urine-modified nucleoside based on surface-enhanced resonance Raman spectroscopy according to claim 7, wherein after the surface-enhanced resonance Raman spectroscopy data of the urine-modified nucleoside of the normal group and the abnormal group of the urine sample of the to-be-detected person is obtained, the posterior probability is calculated through the partial least square and the linear discriminant analysis; and the posterior probability is compared with the threshold to discriminate that the urine sample of the to-be-detected urine-modified nucleoside belongs to the healthy person or belongs to the cancer patient.

9. The detection and analysis method for urine-modified nucleoside based on surface-enhanced resonance Raman spectroscopy according to claim 1, wherein a substitute of the urine-modified nucleoside is a tumor marker in urine, blood, saliva, semen or tissue homogenate.

* * * * *